(12) United States Patent
Nichols et al.

(10) Patent No.: US 9,201,020 B2
(45) Date of Patent: Dec. 1, 2015

(54) SPECIMEN VIEWING DEVICE

(75) Inventors: Mark Eric Nichols, Blooming Prairie, MN (US); Randy Leland Stull, Owatonna, MN (US); Kristin Spurgeon, Brownsdale, MN (US); Henry Lynn Boyum, Waseca, MN (US); Charles Edward Boyer, III, Elysian, MN (US)

(73) Assignee: Apogee Enterprises, Inc., Minneapolis, MN (US)

( * ) Notice: Subject to any disclaimer, the term of this patent is extended or adjusted under 35 U.S.C. 154(b) by 59 days.

(21) Appl. No.: 13/280,807

(22) Filed: Oct. 25, 2011

(65) Prior Publication Data

US 2013/0100549 A1   Apr. 25, 2013

(51) Int. Cl.
| | |
|---|---|
| *G02B 27/00* | (2006.01) |
| *G01N 21/88* | (2006.01) |
| *G02B 27/02* | (2006.01) |
| *G01N 21/958* | (2006.01) |

(52) U.S. Cl.
CPC .......... *G01N 21/8803* (2013.01); *G01N 21/958* (2013.01); *G02B 27/022* (2013.01)

(58) Field of Classification Search
CPC .......... G02B 5/26; G02B 7/00; G02B 27/022; G03B 15/06; G03B 2215/0589; F21V 9/02; F21V 9/08; F21V 9/10; F21V 2009/08
USPC .......... 359/894; 362/7, 16–18, 351, 352, 360, 362/367
See application file for complete search history.

(56) References Cited

U.S. PATENT DOCUMENTS

| | | | |
|---|---|---|---|
| 165,811 A | 7/1875 | Feix | |
| 165,812 A | 7/1875 | Fletcher | |
| 2,239,528 A | 4/1941 | Knudson | |
| 2,739,863 A * | 3/1956 | Ferris | ............................ 312/231 |
| 2,925,634 A | 2/1960 | Ewing | |
| 3,009,389 A | 11/1961 | Ewing | |
| 3,077,643 A | 2/1963 | Carll | |
| 3,120,883 A | 2/1964 | Greilling | |
| 3,236,290 A | 2/1966 | Lueder | |
| 3,260,026 A | 7/1966 | Bacon | |
| 3,324,620 A | 6/1967 | Requena | |
| 3,800,451 A | 4/1974 | Bulkley | |
| 3,846,152 A | 11/1974 | Franz | |

(Continued)

FOREIGN PATENT DOCUMENTS

| | | |
|---|---|---|
| CH | 469 180 | 2/1969 |
| FR | 2 878 844 | 6/2006 |

(Continued)

OTHER PUBLICATIONS

"Impact of Coated Windows on Visual Conception", Marie-Claude Dubois et al., pp. 1-35, Jan. 1, 2003.

(Continued)

*Primary Examiner* — Stephone B Allen
*Assistant Examiner* — James McGee
(74) *Attorney, Agent, or Firm* — Dorsey & Whitney, LLP

(57) ABSTRACT

A specimen viewing device includes an enclosure, a specimen mounting system arranged on the enclosure for receiving the specimen and holding the specimen relative to the enclosure, and a background color control system arranged on the enclosure and configured for controlling a background color of the enclosure. A method of viewing a specimen is also provided.

30 Claims, 5 Drawing Sheets

(56) References Cited

U.S. PATENT DOCUMENTS

| | | | |
|---|---|---|---|
| 4,035,539 | A | 7/1977 | Luboshez |
| 4,316,337 | A | 2/1982 | Da Costa |
| 4,409,960 | A | 10/1983 | Balzer |
| 4,790,922 | A | 12/1988 | Huffer |
| 4,883,721 | A | 11/1989 | Nalepka et al. |
| 4,902,081 | A | 2/1990 | Huffer |
| 5,562,951 | A | 10/1996 | Kamen |
| 5,743,038 | A | 4/1998 | Soto |
| 5,778,258 | A * | 7/1998 | Zamoyski .......................... 396/2 |
| 7,055,976 | B2 * | 6/2006 | Blanford .......................... 362/16 |
| 7,220,019 | B2 * | 5/2007 | Cheung et al. ................ 362/235 |
| 7,654,023 | B2 | 2/2010 | Peters et al. |
| 7,864,264 | B2 | 1/2011 | Sato et al. |
| 7,884,904 | B2 | 2/2011 | Wada |
| 2009/0015924 | A1 | 1/2009 | Mitchell |
| 2009/0139120 | A1 | 6/2009 | Albert |
| 2009/0246476 | A1 | 10/2009 | Mennechez et al. |
| 2010/0244732 | A1 | 9/2010 | Kracht et al. |
| 2010/0308061 | A1 * | 12/2010 | Loulourgas ................ 220/592.2 |
| 2011/0176212 | A1 | 7/2011 | Lu et al. |

FOREIGN PATENT DOCUMENTS

| | | |
|---|---|---|
| GB | 528 796 | 11/1940 |
| WO | WO 2010/053921 | 5/2010 |

OTHER PUBLICATIONS

Viracon, "Insulating Glass Specs & Tech"; date unknown.

* cited by examiner

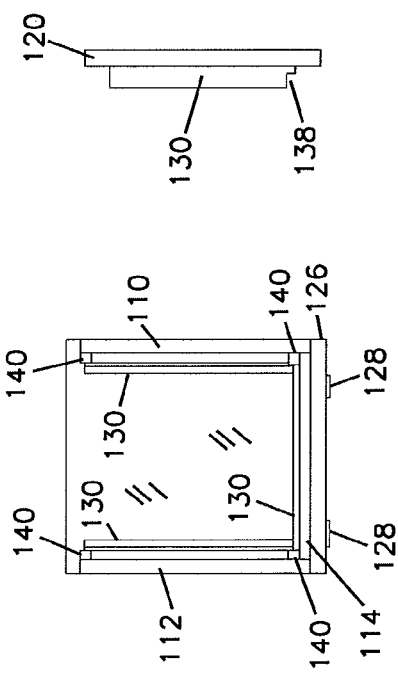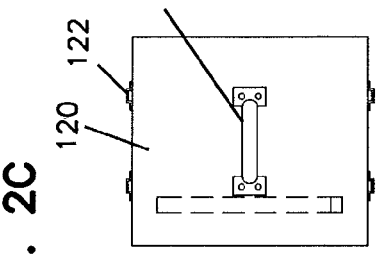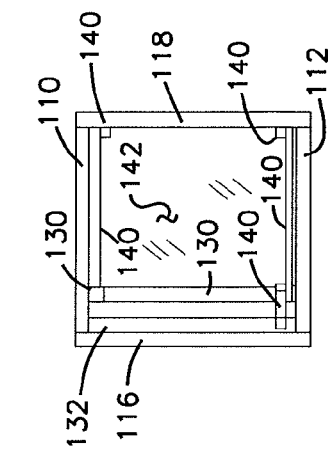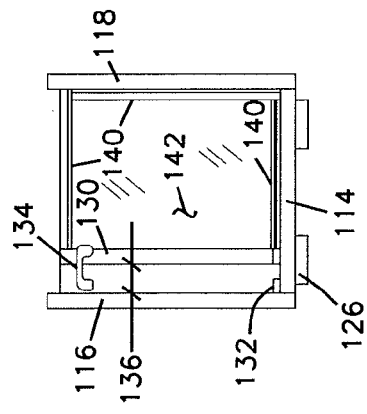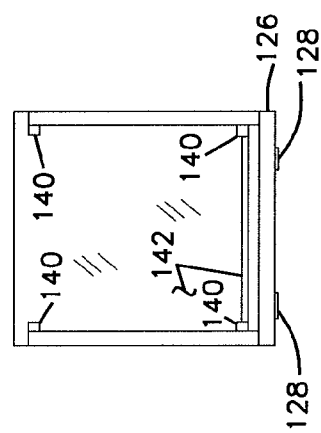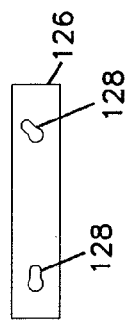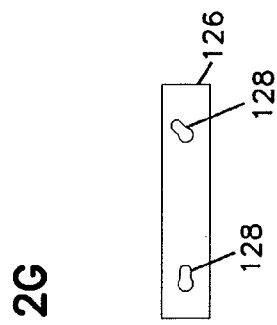

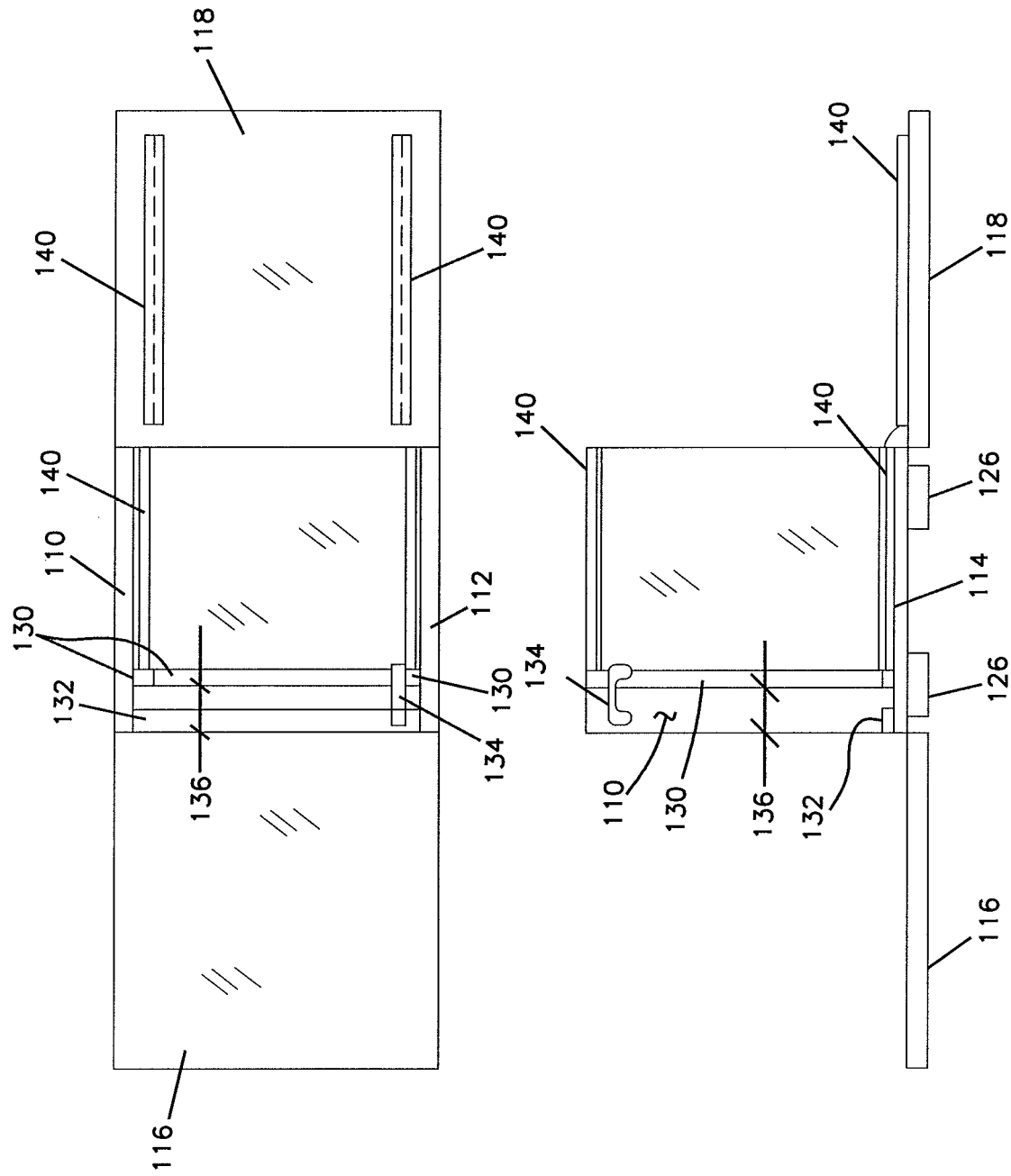

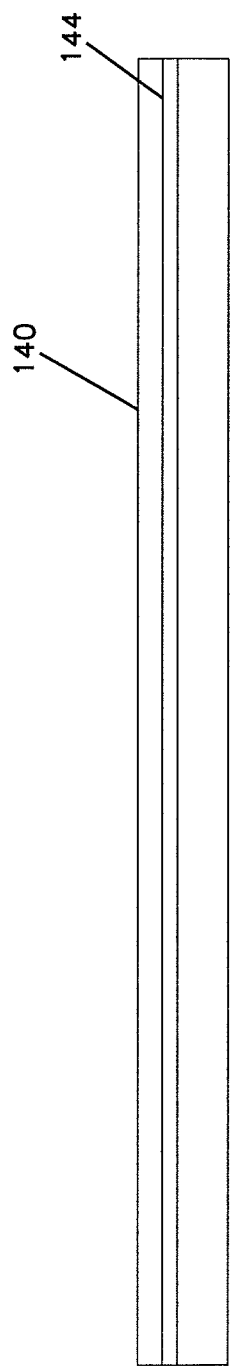
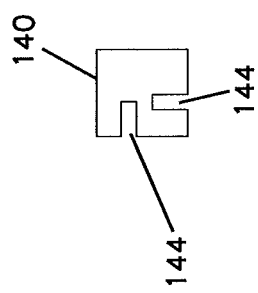
FIG. 5A
FIG. 5B

SPECIMEN VIEWING DEVICE

FIELD OF THE INVENTION

The present application relates to a device for holding specimens for viewing thereof. More particularly, the present application relates to light control viewing devices such as boxes, tubes, tunnels, dished structures, and the like for controlling the light imparted on the specimen. Still more particularly, the present application relates to a light control viewing device for holding and viewing glass such as monolithic panels and/or insulated glass units.

BACKGROUND

Window glass, or raw soda-lime glass, is naturally relatively highly emissive. To improve thermal efficiency (insulation properties), specially designed thin film coatings are often applied to one or more surfaces of the raw soda-lime glass. These coatings reflect radiant infrared energy, thus tending to keep radiant heat on the same side of the glass from which it originated, while letting visible light pass. This results in more efficient windows because radiant heat originating from indoors in winter is reflected back inside, while infrared heat radiation from the sun during summer is reflected away, keeping it cooler inside.

The inward and outward appearance of coated glass can be difficult to anticipate. In addition, the light throughput and the effect thereon can also be difficult to anticipate. Computer modeling programs are often used to attempt to portray the appearance of the coated glass. However, when viewing the portrayal on a computer or printout thereof it can be difficult to obtain an accurate understanding of how the coated glass will appear when actually constructed and in place on a building or other structure.

SUMMARY

In one embodiment, a specimen viewing device may include an enclosure and a specimen mounting system arranged on the enclosure for receiving the specimen and holding the specimen relative to the enclosure. The device may also include a background color control system arranged on the enclosure and configured for controlling a background color of the enclosure.

In another embodiment, a specimen viewing device may include an enclosure defining a cavity, a specimen mounting system configured for securing an at least partially transparent specimen adjacent the cavity, and a background color control system arranged about the cavity for imparting color into the cavity thereby affecting the appearance of the specimen.

In another embodiment, a method of viewing a specimen may include placing the specimen in a specimen viewing device where the device comprises an enclosure and a background color control system. The method may also include selectively adjusting the background color control system and analyzing the appearance of the specimen from one or more vantage points.

It is to be understood that both the foregoing description and the following detailed description are for purposes of example and explanation and do not necessarily limit the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE FIGURES

FIG. 2A is a frontward directed cross-sectional view through the device of FIG. 1.

FIG. 2B is a rearward directed cross-sectional view through the top of the device of FIG. 1.

FIG. 2C is a top view of the top of the device of FIG. 1.

FIG. 2D is a downward directed cross-sectional view through the device of FIG. 1.

FIG. 2E is a leftward directed cross-sectional view through the device of FIG. 1.

FIG. 2F is a rearward directed cross-sectional view through the device of FIG. 1.

FIG. 2G is a bottom view of a spacer of the device of FIG. 1.

FIG. 3A is a top view of the device of FIG. 1 with the top removed and the front and back of the device in an opened position.

FIG. 3B is a leftward directed cross-sectional view thereof.

FIG. 5A is a side view of a mounting element of the device of FIG. 1.

FIG. 5B is an end view thereof.

DETAILED DESCRIPTION

Figure 1:
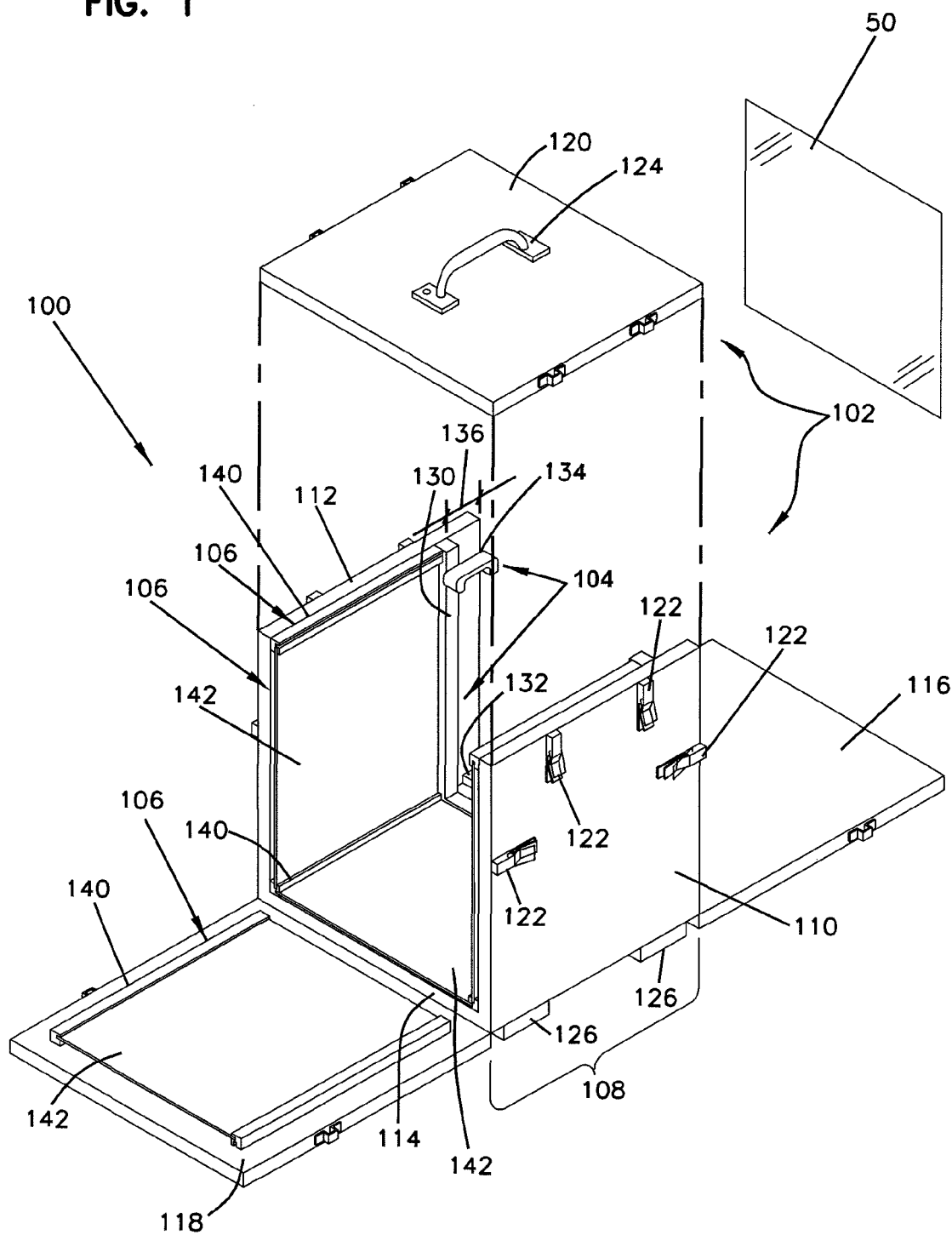
FIG. 1 is a perspective view of a specimen viewing device with an open front, an open back, and a removed top, according to some embodiments.
Figure 4A:
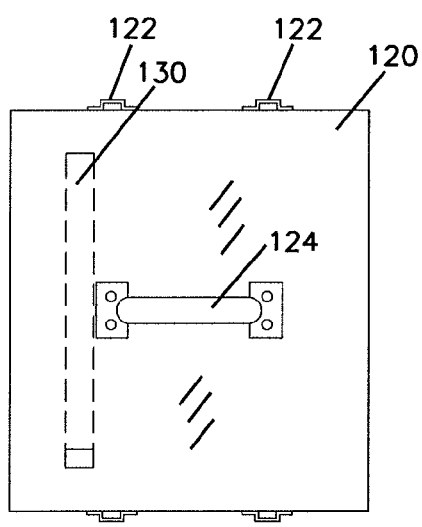
FIGS. 4A and 4B are top views of the device of FIG. 1.
Figure 4B:
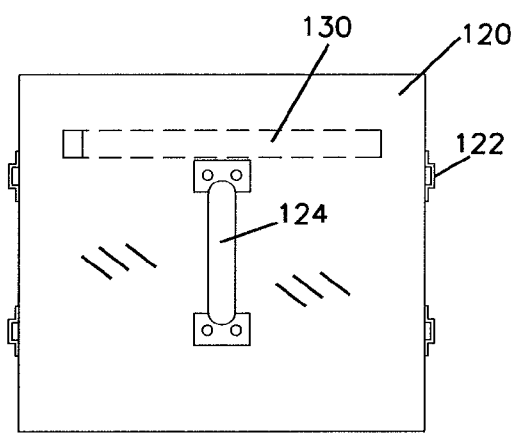
Figure 4C:
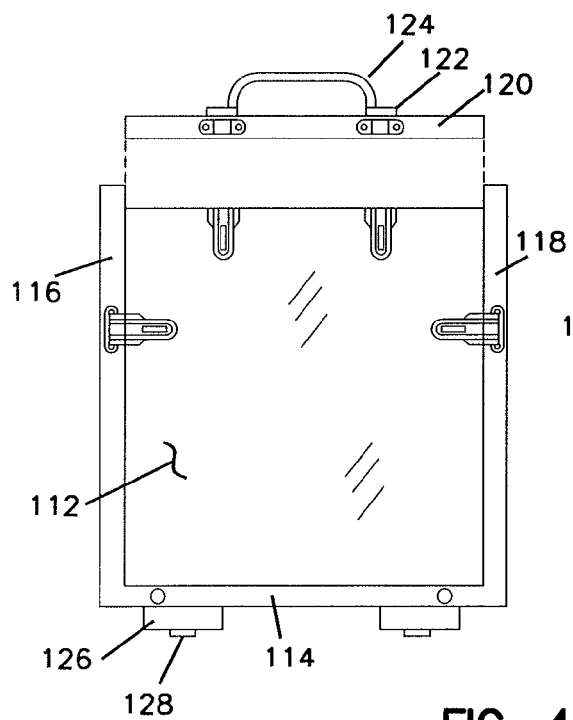
FIGS. 4C and 4D are right and rear views, respectively, of the device of FIG. 1.
Figure 4D:
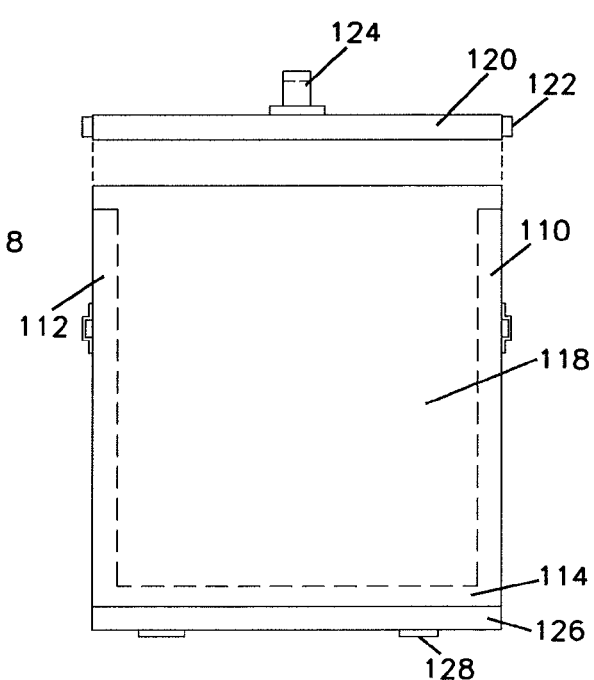
Figure 4E:
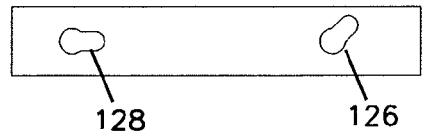
FIG. 4E is a bottom view of a spacer of the device of FIG. 1.

In one embodiment, the present application relates to a light box for placing samples or specimens of coated glass therein. The light box may include a six-sided box where the sample or specimen may be arranged at, near, or just inside one of the sides. The inside of the box may have removable and replaceable panels allowing for the color of the inside of the box to be changed. Several of the sides of the box may be openable. In one embodiment, for example, one or more of the front, back, and top of the box may be selectively opened allowing for viewing of the glass specimen to obtain an understanding of the in situ (e.g., installed) appearance of the glass. That is, for example, when the front of the box is opened, viewing the specimen from outside of the box may resemble the appearance of the in situ glass from the outside of the building or other structure. In another example, when the back of the box is opened, viewing the specimen from the back of the box and through the box may resemble the appearance of the in situ glass from the inside of the building or other structure. The light box may thus be used to study the in situ appearance of different coatings on glass without having to build full size mock ups or fully install the glass.

Several different types of specimens may be used with the described device 100. In some embodiments, monolithic glass may be included. In other embodiments wired glass or RF glass may be included. In still other embodiments, painted glass such as silkscreen, digitally printed, ceramic frit, or other types of painted glass may be included. In another embodiment, clear glass may be included or tinted or colored glass may be included. In still other embodiments, laminated glass or coated glass such as Low E glass, solar reflecting glass, hard coat, soft coat, metal coated, metal/metal oxide coated, or other types of coated glass may be included. In still other embodiments, patterned/textured, acid etched, or sandblasted glass may be included. In still other embodiments insulated glass such as double or triple insulated glass or other levels of insulated glass may be included. In still other embodiments, combinations of the above types of glass may be included on a single specimen and/or the device may be used to compare two or more of these types of glass. In still other embodiments, the specimen viewing device may be used with opaque or semi-opaque specimens. Still other specimen types may also be included.

Referring now to the figures, a specimen viewing device 100 is shown in the form of a six-sided box. As suggested above, the specimen viewing device 100 may be configured to control the angle and/or amount of light imparted on a specimen 50 placed on or in the device 100. As such, while a six-sided box is shown, the specimen viewing device 100 may be in the form of a box, tube, tunnel, dished structure, or other shaped system or device for shading, diffusing, or otherwise controlling the amount and angle of light reaching a specimen. In some embodiments, the device 100 may be a round hat box or boxes with six sides or other numbers of sides such as 7 sides or 5 sides or other numbers greater or less than six sides. In still other embodiments, the device 100 may be a larger or smaller enclosure than that shown and the enclosure may include compartments arranged therein where the compartments are divided with partially or fully separating panels, for example. The walls or panels defining the enclosure or separating panels provided therein may have window-like openings with transparent or opaque shutters which may be sliding, hinged, or otherwise openable or removable shutters allowing for one or more specimen viewing orientations. In some embodiments, a specimen positioning system for mounting a specimen to the device may be stationary or may be adjustable by tilting, rotating, translating, or otherwise adjusting the specimen. In other embodiments, the sides or panels of the device 100 may also be adjustable, by sliding or extending for example, to accommodate different sizes or shapes of specimens. Portions of the device may be moveable, openable, or otherwise adjustable to selectively control the amount of light allowed into the device or imparted on the specimen. In some embodiments, shutter as suggested above may be pivotally, slidingly, rotatably openable or removable. In other embodiments the portions may be similar to shades or blinds or other light limiting devices that may be opened or pivoted to allow a selected amount of light through. In still other embodiments, gas-filled chambers allowing for the opacity of the chamber to be adjusted and thus selectively adjusting the amount of light passing therethrough may also be used. The device may also include a light source for directing internal and/or external light on a specimen or for providing background light for example.

As shown in FIG. 1, the specimen viewing device 100 may include an enclosure 102 for fully and/or partially enclosing a specimen 50 or otherwise controlling the light imparted on the specimen 50. The specimen viewing device 100 may also include a specimen positioning system 104 for locating, orienting, and holding the specimen 50. The specimen viewing device 100 may also include a background color control system 106. Each of these portions of the device will described in detail.

As suggested, the enclosure 102 may be any shape and may be selected based on the type and shape of the specimen and the type of specimen light exposure desired. In the embodiment shown, the enclosure is in the form of a six-sided box 102. The box 102 may be constructed in one of several ways known to those of skill in the art. That is, in one embodiment the box 102 may be made of foldable material and the several sides may be folded to create a box 102. In the embodiment shown, the box 102 is made from relatively rigid material. Some of the sides of the box 102 are connected to one another with relatively rigid connections and other sides of the box 102 are connected with hinged structures allowing the sides to pivot about the hinged connection. Where hinged connections are provided, a system of latches may be provided to secure the respective sides in place and selectively prevent hinged motion.

As shown in FIG. 1, the six-sided box 102 may include a saddle portion 108 with a left side 110, a right side 112, and a bottom 114. The left side 110 and right side 112 may be secured to the bottom 114 at substantially right angles relative thereto. Other angles, depending on the application and purpose of the enclosure 102, may be provided. The left and right sides 110, 112 may be rigidly connected to the bottom 114 so as to maintain their orientation relative to the bottom 114. In one embodiment, the left and right sides 110, 112 may be separate pieces that are rigidly secured to the bottom 114. Depending on the materials used for the box 102, the sides may be secured with fasteners such as nails, screws, or staples, the sides 110, 112 may be welded, or the sides 110, 112 may be adhered to the bottom 114. In other embodiments, the sides 110, 112 and bottom may be molded or otherwise formed as a single piece. For purposes of description, the location of the sides of the box 102 may be defined as follows. When viewing the saddle portion 108 such that the left side 110 is on the left and the right side 112 is on the right and the bottom 114 extends across the bottom from the left side 110 to the right side 112 or vice versa, the following may be said of the remaining sides. The side closest to the viewer may be the front 116, the side opposite the viewer may be the back 118 and the side extending across the top of the from the left to the right side, or vice versa, may be the top 120 of the box.

The front 116, back 118, and top 120 of the six-sided box 102 may be openable sides. As such, each of these remaining sides 116, 118, 120 may be hingedly connected to or removable from the saddle portion 108 of the box 102. The front side 116 of the box 102 may be connected to the bottom side 114 of the saddle portion 108 with a hinge such that the front side 116 may be opened by a hinge action about an axis defined by the front edge of the bottom 114 of the saddle portion 108. Similarly, the back side 118 of the box 102 may be connected to the bottom side 114 of the saddle portion 108 with a hinge such that the back side 118 may be opened by a hinge action about an axis defined by the back edge of the bottom 114 of the saddle portion 108. The top 120 may be removable from the box 102 and may include a series of latches 122 arranged around its perimeter for selectively securing the top of the box 120 to any one or a combination of the front 116, back 118, left 110, and/or right 112 sides. In the embodiment shown, latches 122 are provided for securing the top 120 to the left 110 and right 112 sides, but not the front 116 or back 118 sides. Two latches 122 are shown for securing the top side 120 to the left side 110 and two additional latches 122 are shown for securing the top side 120 to the right side 112. Other quantities and arrangements of latches 122 may be provided.

Latches 122 may also be provided for securing the front 116 and back 118 sides in a closed position. As with the top 120, latches 122 may be provided around the perimeter of each of the front 116 and back 118 sides for selectively securing the front 116 and back 118 sides to any one or a combination of the left 110, right 112, and/or top 120 sides. In the embodiment shown, latches 122 are provided for securing the front 116 and back 118 sides to the left 110 and right 112 sides, but not the top 120. One latch 122 is provided on each of the front 116 and back 118 sides for securing to the left side 110 and one additional latch 122 is provided on each of the front 116 and back 118 sides for securing to the right side 112. Other quantities of latches 122 may be provided.

The particular arrangement of latches 122 shown may be advantageous because it isolates each of the openable sides from one another with respect to each of their respective latch systems. This is because the openable sides are latched or unlatched to the substantially stationary saddle portion 108. As such, any one of the front 116, back 118, and top 120 sides may be unlatched and opened without regard to whether any of the other front 116, back 118, and top 120 sides are open. Other arrangements of latches 122 may also be provided. The latches may be draw latches so as to pull respective portions of the device tightly together when latched and prevent racking or other movement of the latched parts. Other securing devices other than latches may also be provided such as magnets, snaps, or hook and loop for example.

The box 102 may also include a handle 124 arranged on the top side 120 of the box 102 for carrying the box 102. Other handle 124 arrangements may be provided such as a handle 124 on each of the left 110 and right 112 and/or front 116 and back 118 of the box 102 for two handle carrying. The box 102 may also include spacers 126 arranged on the bottom of the box 102. The spacers 126 may include pads 128 for preventing marring of surfaces when the box 102 is placed on a table, lab bench, counter, or other structure, for example. The spacers 126 may also function to accommodate the thickness of the openable front 116 and back sides 118 as they hinge about the bottom side 114. As such, as shown in FIG. 3B for example, the spacers 126 may have thickness equal to or slightly greater than the thickness of each of the front 116 and back sides 118.

The box-type enclosure 102 may also include a specimen positioning system 104. The specimen positioning system 104 may be configured for receiving the specimen 50 and holding the specimen 50 in place relative to the enclosure 102. In some embodiments, the specimen 50 may be shaped and sized to fit into the enclosure 102. That is, where the enclosure 102 is tubular, for example, the specimen 50 may be circular and configured to close off one end of the tube. In other embodiments, a particular opening may be provided for placement of the specimen 50 and the specimen 50 may be sized to fit into or to cover the opening. In the embodiment shown, the specimen 50 used with the system may be substantially rectangular or square to fit into the front side 116 of the light box enclosure 102. As shown in FIGS. 1, 2B-2E, and 3A-3B, the specimen positioning system 104 may thus include a backer system 130 to control how far into the enclosure 102 the specimen 50 may be placed. A keeper element 132 may be provided to hold the specimen 50 against the backer 130 once in place and a latch 134 may be provided to selectively hold the specimen 50 against the backer 130 once in place.

The backer system 130 may include a series of bumpers or bars 130 arranged on an interior surface of each of the left 110, right 112 and bottom 114 sides of the saddle portion 108. The bars 130 may be continuous or intermittent along their respective sides. The bars 130 shown are continuous along the length of their respective left 110, right 112, and bottom 114 sides. The bars 130 may be secured to their respective sides and together may create a narrowed cavity of the enclosure 102 with an abutment surface facing the front of the box 102 against which the specimen may be placed. In some embodiments, the bumpers or bars 130 may be integral with one another to form a U-shaped bumper or bar. In other embodiments, the several portions may be separate from one another. The bars 130 may extend substantially parallel to the front side 116 of the box 102 such that when the specimen 50 is placed against the bars 130, the specimen 50 may be arranged substantially parallel to the front side 116 of the box 102. The bars 130 may be spaced from the front edge of the bottom 114 of the box 102 by an offset distance 136. The offset distance 136 may be substantially equal to the thickness of the specimen 50 plus the thickness of the keeper element 132 described below. Other offset distances 136 may be provided and selected to adjust the depth of the specimen 50 within the enclosure 102. In some embodiments, the offset distance may be adjustable by sliding or otherwise moving the backer system, for example. In still other embodiments, the backer system may be tiltable or pivotable to selectivley adjust the angle and/or orientation of the specimen 50. Other orientations of the bumpers or bars 130 may be provided and selected to best resemble the in situ orientation or sloping angle, for example, of the glass.

The bumpers or bars 130 may have a thickness measured substantially perpendicular to the respective side of the box to which they are attached. The thickness of the bumper or bar 130 may be selected to be the same or similar to the thickness of the mounting elements 140 of the background color control system 106 described below. As such, when viewing from the front, the bumper or bar 130 may substantially blackout the structures associated with the background color control system 106 providing a substantially clean view through the specimen 50 into the box 102, lined with color boards, for example.

As shown in FIGS. 2B and 2C, the backer system 130 may also include an additional bumper or bar 130 arranged on the top side 120 of the box 102. Where the top side 120 of the box 102 is openable, as shown, the bumper or bar 130 on the top side 120 of the box 102 may be separable or separate from the bumpers or bars 130 on the left 110, right 112, and bottom 114 of the saddle portion 108. In some embodiments, the bumper or bar 130 on the top portion 120 may have length less than the width of the top 120 of the box 102, as shown, so as to nest between the bumpers 130 on the left and right side of the box. The bumper 130 on the top side 120 may be spaced from the front side 116 of the box 102 by the same offset distance 136 as the bumpers or bars 130 on the left 110, right 112, and bottom 114 of the box 102 so as to provide a uniform abutment surface around the perimeter of the specimen 50.

The specimen positioning system 104 may also include a keeper element 132. The keeper element 132 may be configured to hold the specimen 50 against the backer system 130. As shown in FIGS. 2E, 3A, and 3B, for example, the keeper element 132 may be in the form of a keeper strip 132 arranged on the bottom side 114 of the box 102 and spaced toward the front of the box 102 from the backer 130. The keeper 132 may be a continuous or intermittent keeper 132 similar to the backer bars or bumpers 130. At least one continuous or intermittent keeper strip 132 may be arranged along the front edge of the bottom side 114 of the box 102. The keeper strip 132 may be spaced from the backer system 130 a distance substantially equal to and slightly greater than the specimen 50 thickness. For example, where the specimen 50 is a single pane of glass, the distance from the backer 130 to the keeper 132 may be approximately equal to the glass thickness. Where, for example, the specimen 50 is an insulated glass unit (IGU), the distance from the backer 130 to the keeper 132 may be approximately equal to the sum of the glass pane thicknesses and the space therebetween. In some embodiments, spacers may be provided for placement between the backing system, 130 and the keeper 132 with the specimen to take-up excess space therebetween. For example, where the specimen thickness is thinner than the space between the backing system 130 and the keeper 132, a spacer may be provided to take-up the remaining space. While the present embodiment shows a keeper element 132 on the bottom 114 of the box 102, in some embodiments, keeper elements 132 may also be provided on the left 110 and right 112 sides of the box 102. As such, the several keeper elements 132 in conjunction with the backer system 130 may provide a slot for inserting and/or removing the specimen 50, for example, from the top. That is, the top side 120 may be removed or opened exposing the top of the slot and the specimen 50 may be inserted by sliding the specimen 50 between the backer system 130 and the keeper elements 132 from the top. In this embodiment, the latch 134 may not be provided since the backer system 130 and keeper element 132 may sufficiently secure the specimen 50.

The specimen positioning system 104 may also include a latch 134. The latch 134 may be configured to allow placement of the specimen 50 and further configured to move into position to secure the specimen 50. In the embodiment shown, the latch 134 is in the form of a hook-shaped element 134. As shown, the hook-shaped element 134 may be pivotable about a pivot pin arranged along the right side backer 130. In some embodiments, the pivot pin may be a screw or through bolt inserted into the side of the backer 130 and arranged generally perpendicular thereto. As such, the hook-shaped element 134 may be moveable in a plane perpendicular to the specimen 50 and parallel to the side backer 130. As shown in FIG. 2B, the top backer 130 may include a space or gap 138 therein for accommodating upward motion of the latch 134 allowing the latch 134 to move upward out of the way of the specimen 50 for insertion and/or removal of the specimen 50. This arrangement of the latch 134 may be advantageous as each of the front 116, back 118, and top 120 of the box 102 may be opened without freeing the specimen 50. Other arrangements of the latch 134 may also be provided. In some embodiments, the latch 134 may be biased toward the closed position to secure the specimen. For example, a spring may be provided to bias the latch 134 to secure the specimen.

While a hook-like latch 134 has been described, other latch systems 134 may be provided. For example, keeper bars 132 may be provided on the left 110 and right 112 sides of the box 102. The keepers 132 may be pivotable, via a hinge for example, about an axis generally aligned with the front edge of the left 110 and right 112 sides and thus pivotably moveable out of the front of the box 102 and out of the way to allow placement of a specimen 50. The keepers 132 may be pivotable back into position once the specimen 50 is placed and may secure each side of the specimen 50 against respective backer bars 130. As with the hook-like latch 134, these keeper-type latches 134 may be biased toward a secured position to hold the specimen 50 in place. Still other latch devices 134 and systems may be used with the specimen positioning system 104 such as rotatable tabs similar to those found on the back of a picture frame for keeping the backing of a picture frame in place. Still other systems may be used.

While the specimen positioning system 104 has been described to include a series of backers 130, a keeper 132, and a latch 134, other specimen positioning systems 104 may be provided. For example, magnets may be used to secure the specimen 50. In still other embodiments, adhesives may be used. In either of these embodiments, the adhesives or magnets may be used to secure the specimen 50 to the edge of the saddle portion 108, for example, or backers 130 may be used and the adhesives or magnets may be used to secure the specimen 50 thereto. In still other embodiments, the specimen may be friction fit into or onto the enclosure 102. Still other specimen positioning systems 104 may be provided.

The background color control system 106 may be configured for controlling the color of the inside of the enclosure 102. The color of the inside of the enclosure 102 may thus be selectively changed using the background color control system 106 to help the user understand the relationships between color and the specimen 50. That is, the background color may have an effect on the appearance of the specimen 50 from some vantage points and the specimen 50 may have an effect on the appearance of the background color from some vantage points. As shown in FIG. 1, the background color control system 106 may include a plurality of mounting elements 140 and a plurality of colored cassettes 142 for mounting on the mounting elements 140. The mounting elements 140 may be configured to allow for insertion, removal, and replacement of the colored cassettes 142 to allow the internal colors of the enclosure 102 to be selectively modified. It is noted that while a physical and manually changeable background color control system 106 is described, an electronic system may also be provided where the sides of the enclosure 102 include color modifiable panels such as liquid crystal or other screens allowing for changing the color electronically and/or automatically.

In the embodiment shown, the mounting elements 140 may be in the form of mounting strips 140 for receiving the colored cassettes 142. As shown in FIGS. 5A and 5B, the mounting strips 140 may be substantially square or rectangular in cross-section and may be relatively elongate. The mounting strips 140 may have slots 144 extending along their length. The slots 144 may be configured to receive an edge of a cassette 142 and may thus have a thickness approximately equal to and slightly larger than the thickness of the cassettes 142. The slots 144 may have a depth extending partially through the thickness of the mounting element strips 140. As shown in FIG. 5B each mounting strip 140 may have two slots 144 arranged such that the cross-section of the slots 144 are substantially perpendicular to one another. It is noted that the slots 144 are arranged in cross-section of the mounting strip 140 so as to avoid intersection with one another. That is, at least one of the slots 144 may be offset from the center of the respective face of the strip 140 through which it is cut allowing for the slot 144 on the adjacent face to avoid intersection therewith. Where the slot 144 depth extends into the mounting strip such that the slot begins to encroach the slot 144 on an adjacent surface, this offset may allow the slots 144 to avoid intersection. In some embodiments, the slot depth may be adjusted (i.e., made smaller) to allow the slots 144 to be positioned on the center of the respective face of the strip 140 of which they are cut or more toward the internal corner thereof.

Referring again to FIG. 1, the mounting strips 140 may be arranged in the saddle portion 108 of the enclosure 102 to receive four cassettes 142. One mounting strip 140 may be arranged at the intersection of the bottom side 114 and the left side 110 and may extend along the intersection thereof. An additional mounting strip 140 may be arranged at the intersection of the bottom side 114 and the right side 112 and may extend along the intersection thereof. Still another mounting strip 140 may be arranged near the top edge of the left side 110 and may extend along the top edge thereof. Yet another mounting strip 140 may be arranged near the top edge of the right side 112 and may extend along the top edge thereof. Additional mounting strips 140 may be arranged on the back side 118 of the enclosure 102 to receive a fifth cassette 142. These latter mounting strips 140 may be arranged to extend upward along the back side 118 and may be spaced in from the vertical edges of the back side 118 such that the mounting strips 140 on the back side 118 fall within the boundary defined by the inside face of the mounting strips 140 on the saddle portion 108. As such, when the back side 118 is closed, the mounting strips 140 positioned thereon may avoid interfering with the mounting strips 140 on the saddle portion 108. The mounting strips 140 on the back side 118 may also be oriented such that only one of the slots 144 therein is exposed and the remaining slot 144 is facing the back side 118 of the enclosure 102. This is because these mounting strips 140 may not receive cassettes 142 from adjoining sides of the enclosure 102. The mounting strips 140 on the back side 118 may also be arranged to extend across the back side 118 rather than upward. When all five cassettes are installed, and the enclosure 102 is fully closed, a view through the specimen 50 may show a substantially rectangular or square box having a top 120, a bottom 114, a left side 110, a right side 112, and a back wall 118 with a color matching that of the respective colored cassette 142.

The cassettes 142 may be relatively thin elements configured for sliding in the slots 144 of the mounting strips 140 and configured for selective insertion and removal from the slots 144 of the mounting strips 140. The cassettes 142 may be plate-like elements, for example. The cassettes 142 may include two surfaces having the same or differing colors applied thereto. As such, the cassettes 142 may be reversible allowing for alternative colors to be analyzed with a single set of cassettes 142. The cassettes 142 may be relatively rigid and configured for spanning from one mounting strip 140 across the enclosure to another mounting strip 140. The cassettes 142 may be wood, metal, paperboard, cardboard, plastic, stretched fabric, or composite materials may be used. Other materials may also be used. It is also noted that while slotted mounting strips and cassettes have been described other systems for adjusting the background color may also be provided. For example, magnetic mounting strips, or mounting strips having hook and loop, snaps, or other re-usable fasteners may be used.

A light source may also be provided in the enclosure 102. For example, rope lights, incandescent bulbs, fluorescent bulbs, LED's, halogen bulbs, or other lighting may be provided. For example, LED lighting may be provided along the exposed portion of the mounting strips 140 to "wash" the cassettes 142 with light and provide internal lighting to the enclosure 102. In other embodiments, lighting may be provided on the internal side of the backer bars 130 to flood the enclosure 102 with light. Other locations and types of lighting may also be provided to allow the internal volume of the enclosure 102 to be lit. External lighting may also be provided to shine light on the exterior face of the specimen 50, for example, and thus analyze reflectivity and other attributes of the specimen 50.

The several parts of the specimen viewing device 100 may provide an enclosure 102 for positioning of an at least partially transparent specimen 50 thereon. The enclosure 102 may provide a cavity or empty volume on at least one side of the specimen 50 and the background color control system 106 may impart color into the cavity or empty volume by providing colored cassettes surrounding or adjacent to the cavity or empty volume. As such, the specimen viewing device may resemble the effect of a painted or otherwise colored space within a building on the appearance of the glass separating the space from the outdoors or another space. This ability to model the appearance of glass or glazing in conjunction with the other aspects of a building that may affect this appearance may be advantageous in more accurately understanding and/or conveying an understanding of the anticipated appearance of a glass or film coated glass.

In some embodiments, the device 100 may be configured to allow side-by-side viewing of specimens. In some embodiments, the device may be sized to receive two specimens adjacent to one another. Accordingly, the two specimens may be placed in the device 100 and comparisons may be made of the effect of similar exposures on differing specimens, for example. In some embodiments, provisions for a center wall may be provided allowing for the adjacent specimens to have similar exposure conditions along all sides. As such, differing specimens with identical or nearly identical background and/or lighting conditions may be compared side-by-side. Additionally, side-by-side comparisons of the identical or nearly identical specimens may be made where the background colors and/or lighting are different. In still other embodiments, multiple viewing devices 100 may be used and may be placed adjacent to one another for similar viewing comparisons.

In use, the specimen viewing device 100 may allow for viewing of glass or coated glass or other specimens 50. When starting with a fully closed enclosure 102, the front side 110 may be opened and a specimen 50 may be placed. The specimen 50 may be tipped slightly to place the bottom of the specimen 50 behind the keeper element 132 on the bottom side 114 of the box 102 and between the keeper element 132 and the backer bar 130. The specimen 50 may be tipped into place against the remaining backer bars 130, on the left 110 and right 112 side and top 120 of the enclosure 102 for example, and the latch 134 may be pivoted into position to hold the specimen 50 in place. Where cassettes 142 are already in place, the specimen 50 may be viewed from the front 116. Where lighting is provided in the enclosure 102 the lighting may be turned on or off to review the effect of the light on the specimen 50 in conjunction with the color of the cassettes 142. Viewing from the front 116 in this condition may resemble the appearance of the specimen 50 from the outside of a building, for example, with lights on or off inside the building. Where cassettes 142 are to be installed or changed, the back 118 of the enclosure 102 may be unlatched and opened. A color or pattern of colors for the cassettes 142 may be selected and cassettes 142 for the sides 110, 112, bottom 114 and top 120 may be installed into the mounting strips 142 via sliding in the slots 144 thereof from the back 118 of the enclosure 102. A cassette 142 for the back 118 of the enclosure 102 may be slid into the slots 144 of the mounting strips 142 positioned on the back side 118 of the enclosure 102. The back side 118 of the enclosure 102 may be closed with the new cassettes 142 in place or the back 118 may be left open to allow light in the enclosure 102 or to allow outward viewing of the specimen 50 from the inside of the enclosure 102. Outward viewing from the back 118 through the enclosure 102 may resemble the appearance of the specimen 50 from the inside of a building for example. In some cases, the top cassette 142 may be removed and the top side 120 of the enclosure 102 may also be removed to allow light to enter the enclosure 102 from above. The specimen 50 may then be viewed from the front 118 or the back 118 (if the back remains open) to analyze the specimen 50. Other combinations of open sides and vantage point viewing may also be performed.

For purposes of transport, the specimen 50 may be removed or the specimen 50 may remain in place in the enclosure. The front 116, back 118, and top 120 of the enclosure may be closed and latched and the enclosure 102 may be carried via the handle 124 or other carrying system.

While the present disclosure has been described with reference to various embodiments, including preferred embodiments, it will be understood that these embodiments are illustrative and that the scope of the disclosure is not limited to them. Many variations, modifications, additions, and improvements are possible. Functionality may be separated or combined in blocks differently in various embodiments of the disclosure or described with different terminology. These and other variations, modifications, additions, and improvements may fall within the scope of the disclosure as defined in the claims that follow.

What is claimed is:

1. A specimen viewing device, comprising:
   an enclosure comprising
      a stationary saddle portion comprising a bottom, a first side, and a second side; and
      openable portions comprising a front side, a top side, and a back side for selectively opening or closing one or more of the openable portions, the openable portions being selectively latched or unlatched to the saddle portion by an arrangement of latches configured to isolate each of the openable portions from one another;
   a specimen mounting system arranged on the enclosure for receiving the specimen and holding the specimen relative to the saddle portion; and
   a background color control system arranged on the saddle portion and configured for controlling a background color of the enclosure,
   wherein the device is configured to enable a viewer to view the specimen through the device by selectively opening one or more of the openable portions.

2. The device of claim 1, wherein the enclosure is in a form of a box.

3. The device of claim 1 wherein the latches are draw latches, magnets, snaps, or hook and loop.

4. The device of claim 1 wherein the specimen mounting system is stationary.

5. The device of claim 1 wherein the specimen mounting system is adjustable by tilting, rotating, or translating.

6. The device of claim 1, wherein the specimen mounting system includes a backer system and a keeper system.

7. The device of claim 6, wherein the specimen mounting system includes a latch system for selectively securing the specimen.

8. The device of claim 1, wherein the background color control system includes a plurality of cassettes configured for selectively placing within the enclosure.

9. The device of claim 8, wherein the background color control system includes a plurality of mounting elements for receiving the cassettes.

10. The device of claim 9, wherein the mounting elements include elongate strips having slots extending therealong.

11. The device of claim 10, wherein the cross-section of the slots in the strips are arranged to be substantially orthogonal to one another.

12. The device of claim 10, wherein the a portion of the mounting elements are configured to receive cassettes by sliding the cassettes in the slots of the strips from the back of the device.

13. The device of claim 1, further comprising a specimen mounted to the specimen mounting system.

14. The device of claim 13, wherein the specimen comprises glass.

15. The device of claim 14, wherein the specimen comprises monolithic glass.

16. The device of claim 14, wherein the specimen comprises painted glass.

17. The device of claim 14, wherein the specimen comprises coated glass.

18. The device of claim 17, wherein the coated glass comprises one or more of a hard coat, a soft coat, a metal coat, or a metal/metal oxide coat.

19. The device of claim 14, wherein the specimen comprises an insulated glass unit.

20. The device of claim 19, wherein the insulated glass unit is a laminated insulated glass unit.

21. A method of viewing a specimen, comprising:
   mounting a specimen in the specimen mounting system of the specimen viewing device of claim 1;
   adjusting the background color control system;
   selectively opening one or more of the openable portions; and
   analyzing an appearance of the specimen through the device.

22. The method of claim 21, wherein selectively opening one or more of the openable portions comprises unlatching an openable portion and hingedly moving the openable portion.

23. The method of claim 21, wherein selectively opening one or more of the openable portions comprises unlatching an openable portion and removing the openable portion from the enclosure.

24. The method of claim 21, wherein selectively adjusting the background color control system comprises selectively inserting colored cassettes into the enclosure.

25. The method of claim 24, wherein selectively inserting colored cassettes into the enclosure comprises selectively sliding cassettes into mounting elements arranged on the enclosure.

26. The method of claim 21, wherein the specimen comprises glass.

27. The method of claim 26, wherein the specimen comprises monolithic glass.

28. The method of claim 26, wherein the specimen comprises painted glass.

29. The method of claim 26, wherein the specimen comprises coated glass.

30. The method of claim 26, wherein the specimen comprises an insulated glass unit.

* * * * *